United States Patent [19]

Nomoto et al.

[11] 4,331,606

[45] May 25, 1982

[54] N-(SUBSTITUTED CHROMONE-3-CARBONYL)-PHENYLGLYCINE DERIVATIVES

[75] Inventors: Seiichiro Nomoto; Hironori Ikuta, both of Tokyo; Yoshimasa Machida, Wako; Shigeto Negi, Kodaira; Isao Sugiyama, Tokyo; Hiroshi Yamauchi, Gifu; Takeo Kanai, Honjo; Isao Saito, Sakura, all of Japan

[73] Assignee: Eisai Co., Ltd., Tokyo, Japan

[21] Appl. No.: 218,404

[22] Filed: Dec. 19, 1980

[30] Foreign Application Priority Data

Aug. 11, 1980 [JP] Japan ............................ 55/109161

[51] Int. Cl.$^3$ ........................................... C07D 311/24
[52] U.S. Cl. ....................................... 549/402; 544/27
[58] Field of Search ..................................... 260/345.2

[56] References Cited

U.S. PATENT DOCUMENTS 3,904,618  9/1975  Pioch ............................... 260/345.2
3,984,441 10/1976  Nohara et al. ................... 260/345.2

FOREIGN PATENT DOCUMENTS 49-32860  9/1974  Japan ............................. 260/345.2

Primary Examiner—Nicky Chan
Attorney, Agent, or Firm—Wenderoth, Lind & Ponack

[57] ABSTRACT

N-(Substituted chromone-3-carbonyl)phenylglycine derivatives. These derivatives are useful intermediates for cephem compounds which are excellent as antibacterial agents.

5 Claims, No Drawings

N-(SUBSTITUTED CHROMONE-3-CARBONYL)-PHENYLGLYCINE DERIVATIVES

This invention relates to novel N-(substituted chromone-3-carbonyl)phenylglycine derivatives of the following formula:

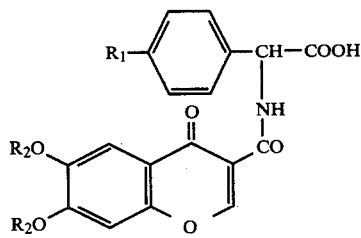
(I)

in which $R_1$ represents a hydrogen atom or a hydroxyl group, and $R_2$ represents a hydrogen atom, an alkoxycarbonyl group or a chlorine-substituted alkoxycarbonyl group.

In the formula (I), the alkoxycarbonyl group of $R_2$ includes a methoxycarbonyl group, an ethoxycarbonyl group, a propoxycarbonyl group or the like, and the chlorine-substituted alkoxycarbonyl group includes 2,2,2-trichloroethoxycarbonyl group or the like.

Novel compounds represented by the following formula:

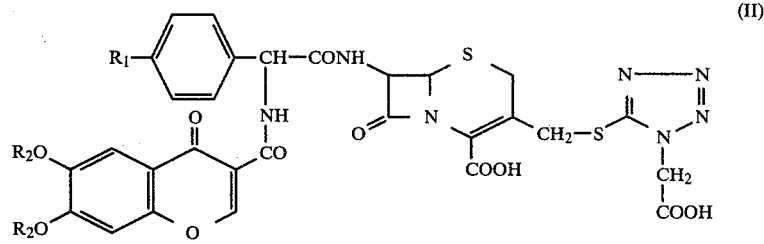
(II)

in which $R_1$ and $R_2$ each has the same meanings as defined above and their salts are excellent as antibacterial agents.

The compounds according to the invention are useful as an intermediate for the compounds of the above formula (II). That is, the compounds of the invention can be used to give the compounds of the formula (II) in accordance with the following procedure:

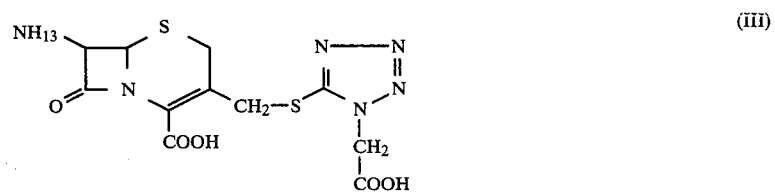
(III)

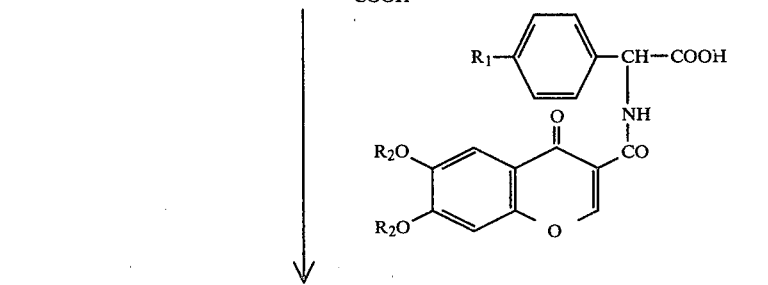

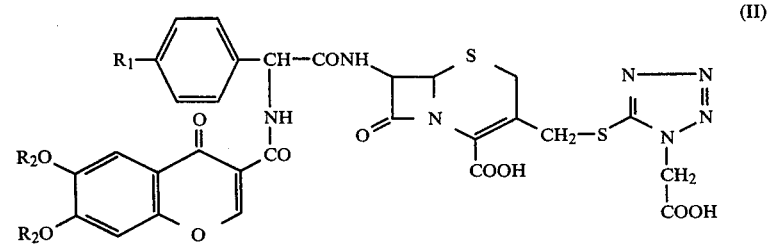
(II)

The compounds of the invention can be prepared by the following method. A compound of the following formula:

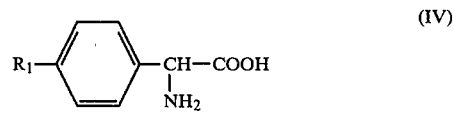
(IV)

in which R₁ has the same meaning as defined hereinbefore is reacted with a compound of the formula:

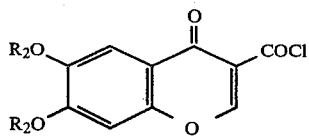

in which R₂ has the same meaning as defined hereinbefore to obtain the compound of the formula:

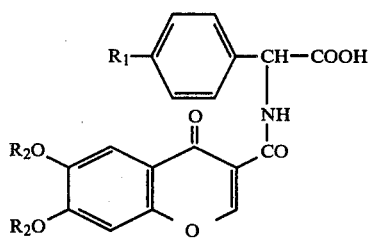

in which R₁ and R₂ have the same meanings as defined hereinbefore, respectively.

The above reaction can be effected in an inert solvent such as dichloromethane, tetrahydrofuran, ethyl acetate, acetonitrile or the like, in the presence or absence of a silylating agent at temperatures below room temperature. Examples of the silylating agent used for the reaction include N,O-bis(trimethylsilyl)acetamide, hexamethyldisilazane, N-trimethylsilylacetamide and the like.

The starting compound of the general formula (V) can be obtained by a procedure which comprises preparing chromone aldehyde by a method such as disclosed in Japanese patent Publication No. 49-32860, oxidizing the chromone aldehyde with an oxidizing agent such as Jones' reagent or sodium chlorite-sulfamic acid, and halogenating the resulting chromonecarboxylic acid by means of thionyl chloride, phosphorus pentachloride or the like.

The present invention is described in more detail by way of the following examples and Preparatory Examples.

PREPARATORY EXAMPLE 1

(A) 6,7-Bis(ethoxycarbonyloxy)chromone-3-carboxyaldehyde (1) 4,5-Bis(ethoxycarbonyloxy)-2-hydroxyacetophenone 2,4,5-trihydroxyacetophenone (3.36 g) was dissolved in 150 ml of ethyl acetate, and 3.24 ml of pyridine was added at about $-5°$ C. with stirring. Then, 50 ml of a solution of 3.8 ml of ethyl chloroformate in ethyl acetate was added dropwise over 30 minutes. The mixture was stirred for 10 minutes at the same temperature. The resulting precipitate was collected by filtration and washed three times with 10 ml of ethyl acetate. The washings and the filtrate were combined, and the mixture was washed with water (once) and a saturated aqueous solution of sodium chloride (three times) and dried over magnesium sulfate. The solvent was distilled off, and the residue was recrystallized from ethyl etherethanol. The crystals were collected by filtration, and washed with ethanol and n-hexane and dried to afford 4.60 g of the desired product.

Melting Point: 58°-60° C.

(2) 6,7-Bis(ethoxycarbonyloxy)chromone-3-carboxyaldehyde

The above compound (1) (37.47 g) was dissolved in 300 ml of dimethyl formamide. The solution was cooled to about $-5°$ C. and with stirring, 120 ml of phosphorus oxychloride was added dropwise over 40 minutes. The mixture was stirred at room temperature for 5.5 hours. The reaction mixture was added to 3 liters of ice water, and stirred for 20 minutes. The resulting precipitate was collected by filtration, washed with water, and dissolved in ethyl acetate. The ethyl acetate layer was washed with water three times and dried over magnesium sulfate. The solvent was distilled off, and ethanol was added to the residue to triturate it. The triturated product was collected by filtration, washed with ethanol and n-hexane, and then dried to afford 28.5 g of the desired product.

Melting Point: 101°-102° C.

Mass Spectrum (m/e): 350 (M+)

Elemental analysis for $C_{16}H_{14}O_9$:

|  | C | H |
|---|---|---|
| Calculated (%): | 54.86 | 4.03 |
| Found (%): | 54.70 | 3.81 |

Infrared Absorption Spectrum (cm⁻¹, nujol): 1775, 1765, 1700, 1660, 1625.

NMR Spectrum (δ, CDCl₃): 1.45 (6H, t, J=7 Hz), 4.40 (4H, q, J=7 Hz), 7.62 (1H, s), 8.17 (1H, s), 8.53 (1H, s), 10.33 (1H, s)

(3) 6,7-Bis(ethoxycarbonyloxy)chromone-3-carboxylic acid

The compound (1.05 g) obtained in (2) was dissolved in 31.5 ml of dichloromethane, and a solution of 1.05 g of sulfamic acid in 18.9 ml of water was added at 10° C. with stirring. Then, a solution of 525.6 mg of sodium chlorite in 1.2 ml of water was added. The solution was stirred at the same temperature for 1 hour, and allowed to separate. The dichloromethane layer was washed with water (once) and then with a saturated aqueous solution of sodium chloride (twice), and dried over magnesium sulfate. The solvent was distilled off, and ethyl ether was added to the residue to solidify it. The solidified product was collected by filtration, and dried to afford 950 mg of the desired product.

Melting Point: 107°-109° C.

Mass Spectrum (m/e): 366 (M+)

Elemental analysis for $C_{16}H_{14}O_{10}$:

|  | C | H |
|---|---|---|
| Calculated (%): | 52.47 | 3.85 |
| Found (%): | 52.57 | 3.63 |

Infrared Absorption Spectrum (cm⁻¹, nujol): 1765, 1625.

NMR spectrum (δ, CDCl₃): 1.38 (6H, t, J=7 Hz), 4.37 (4H, q, J=7 Hz), 7.74 (1H, s), 8.21 (1H, s), 8.98 (1H, s).

(4) 6,7-Bis(ethoxycarbonyloxy)chromone-3-carbonyl chloride

The compound (3) (1.1 g) was dissolved in 20 ml of benzene, and 2 ml of thionyl chloride was added dropwise at room temperature with stirring. Then, the mixture was refluxed with stirring. The reaction mixture was concentrated, and n-hexane was added to the concentrate to crystallize it. The resulting crystals wer collected by filtration, washed with n-hexane and dried to afford 980 mg of the desired product.

Melting Point: 89°–92° C.

Mass Spectrum (m/e): 384 (M+), 386 (M+).

Infrared Absorption Spectrum (cm$^{-1}$, nujol): 1770, 1680, 1620, 1565.

The following compounds are produced in the same manner as mentioned above, except that 6,7-dihydroxychromone-3-carbonyl chloride is obtained by hydrolyzing 6,7-diacetoxychromone-3-carboxylic acid to give 6,7-dihydroxychromone-3-carboxylic acid, and reacting the same with thionyl chloride.

(B) 6,7-Dihydroxychromone-3-carbonyl chloride

Infrared Absorption Spectrum (cm$^{-1}$, nujol): 1780, 1765, 1645, 1625

(C) 6,7-Bis(2,2,2-trichloroethoxycarbonyloxy)chromone-3-carbonyl chloride

Infrared Absorption Spectrum (cm$^{-1}$, nujol): 1765, 1655, 1620, 1565

Melting Point: 140°–142° C.

EXAMPLE 1

D-2-(6,7-Dihydroxychromone)-2-(4-hydroxyphenyl)acetic acid

D(-)-α-(4-Hydroxyphenyl)glycine (16.2 g) was suspended in 240 ml of acetonitrile, to which was added 30 ml of N,O-bis(trimethylsilyl)acetamide, followed by stirring for 30 minutes. Then, 20 g of 6,7-dihydroxychromone-3-carbonyl chloride was added to the reaction solution, followed by agitating for 2 hours at room temperature. To the reaction solution was added 80 ml of 6 N hydrochloric acid under ice-cooling conditions. The resulting yellowish white crystals were filtered off, washed with water, acetonitrile and then isopropyl ether, and dried to obtain 22.7 g of the intended product.

Melting Point: 260°–265° C. (decomposed).

Infrared Absorption Spectrum (cm$^{-1}$, nujol): 1730, 1650, 1640, 1600

NMR Spectrum (δ, DMSO-d$_6$): 5.37 (1H, d, J=7 Hz), 6.76 (2H, d, J=8.5 Hz), 6.94 (1H, s), 7.21 (2H, d, J=8.5 Hz), 7.37 (1H, s), 8.80 (1H, s), 9.41 (1H, br.s), 9.96 (1H, br.s), 10.20 (1H, d, J=7 Hz), 10.62 (1H, br.s)

EXAMPLE 2

D-2-[6,7-Bis(ethoxycarbonyloxy)chromone-3-carboxamido]-2-phenylacetic acid

D(-)-α-Phenylglycine (302.3 mg) was suspended in 50 ml of acetonitrile, to which was further added 0.5 ml of N,O-bis(trimethylsilyl)acetamide at room temperature with stirring. After having been stirred for further 10 hours at room temperature, the reaction solution was ice-cooled, followed by adding 769.4 mg of 6,7-bis(ethoxycarbonyloxy)chromone-3-carbonyl chloride with stirring. The solution was subsequently stirred for 30 minutes at the same temperature and then for further 1 hour after having been returned to room temperature. The solvent was removed by distillation and the residue was charged into 400 ml of ice-cooled 0.4 N hydrochloric acid. The resulting precipitate was collected by filtration and washed with water. The precipitate was dissolved in 300 ml of ethyl acetate, washed three times with a saturated saline solution, and dried over magnesium sulfate. The solvent was removed by distallation and the residue was washed first with ethanolethyl ether and then ethyl ether and dried to obtain 542 mg of the intended product.

Melting Point: 173°–175° C.

Infrared Absorption Spectrum (cm$^{-1}$, nujol): 1770, 1735, 1720, 1660

NMR Spectrum (δ, DMSO-d$_6$): 1.31 (6H, t, J=7 Hz), 4.30 (4H, q, J=7 Hz), 5.53 (1H, d, J=7 Hz), 7.3–7.5 (5H, m), 8.01 (1H, s), 8.17 (1H, s), 9.03 (1H, s), 10.04 (1H, d, J=7 Hz),

EXAMPLE 3

D-2-[6,7-Bis(ethoxycarbonyloxy)chromone-3-carboxamido]-2-(4-hydroxyphenyl)acetic acid D(-)-α-(4-Hydroxyphenyl)glycine (451 mg) was suspended in 20 ml of acetonitrile, to which was added 0.8 ml of N,O-bis(trimethylsilyl)acetamide at room temperature under agitation. After having been agitated overnight at room temperature, the reaction solution was ice-cooled, to which was added 1.774 g of 6,7-bis(ethoxycarbonyloxy)chromone-3-carbonyl chloride under agitation. The solution was further agitated at the same temperature for 2 hours and then at room temperature for 30 minutes. The solvent was removed by distillation and the residue was charged into 100 ml of 0.5 N hydrochloric acid. The mixture was extracted with ethyl acetate and the extract was washed with water and then dried over magnesium sulfate. The solvent was distilled off and the resulting residue was solidified by addition of chloroform. The solidified matter was collected by filtration, washed first with chloroform and then ethyl ether, and dried to obtain 412 mg of the intended product. In addition, 41.5 mg of the intended product was also obtained from the filtrate by crystallization.

Melting Point: 195°–198° C.

Infrared Absorption Spectrum (cm$^{-1}$, nujol): 1775, 1665, 1605, 1560, 1530, 1510

NMR Spectrum (δ, DMSO-d$_6$): 1.31 (6H, t, J=7 Hz), 4.30 (4H, q, J=7 Hz), 5.39 (1H, d, J=7 Hz), 6.76 (2H, d, J=8 Hz), 7.22 (2H, d, J=8 Hz), 8.00 (1H, s), 8.16 (1H, s), 9.03 (1H, s), 9.47 (1H, s), 9.88 (1H, d, J=7 Hz)

EXAMPLES 4

D-2-[6,7-Bis(2,2,2-trichloroethoxycarbonyloxy)chromone-3-carboxamido]-2-(4-hydroxyphenyl)acetic acid D(-)-α-(4-Hydroxyphenyl)glycine (334.3 mg) was suspended in 50 ml of acetonitrile, to which was added 0.6 ml of N,O-bis(trimethylsilyl)acetamide at room temperature under agitation, followed by agitating for further 14 hours. The solution was ice-cooled, to which was added 1183 mg of 6,7-bis(2,2,2-trichloroethoxycarbonyloxy)chromone-3-carbonyl chloride, followed by agitating at the same temperature for 1 hour and then at room temperature for further 1 hour. The solvent was distilled off and the residue was dissolved in 5 ml of methanol. The solution was charged into 20 ml of ice-cooled 0.1 N hydrochloric acid and agitated for 10 minutes. The resulting precipitate was collected by filtration and washed with water. The thus washed precipitate was dissolved in ethyl acetate, washed with water, and then dried by the use of magnesium sulfate. The solvent was distilled off from the solution. The resulting residue was dissolved in chloroform and purified by column chromatography (solvent: chloroform 483, methanol 15, formic acid 2) using silica gel to obtain 157.2 mg of the intended product.

Melting Point: 190°–192° C.

Infrared Absorption Spectrum (cm$^{-1}$, nujol): 1790, 1780, 1670, 1610

NMR Spectrum (δ, DMSO-d₆): 5.10 (2H, s), 5.11 (2H, s), 5.40 (1H, d, J=7 Hz), 6.77 (2H, d, J=8 Hz), 7.23 (2H, d, J=8 Hz), 8.17 (1H, s), 8.32 (1H, s), 9.07 (1H, s), 9.53 (1H, s), 9.88 (1H, d, J=7 Hz)

PREPARATORY EXAMPLE 2

Preparation of Cephem Derivative (A) 7β-[D-2-{6,7-bis(ethoxycarbonyloxy)chromone-3-carboxamido}-2-(4-hydroxyphenyl)acetamido]-3-[(1-carboxymethyl-5-tetrazolyl)thiomethyl]-3-cephem-4-carboxylic acid (Solution A)

The compound (51.5 mg) obtained in Example 3 was dissolved in 2 ml of dimethylformamide, to which was added ethylchloroformate (10 μl) at −45° C. with stirring, followed by addition of N-methylmorpholine (12 μl). The mixture was stirred for 1 hour at the same temperature.

(Solution B)

7β-Amino-3-[(1-carboxymethyl-5-tetrazolyl)-thiomethyl]-3-cephem-4-carboxylic acid (55.8 mg) was suspended in 1.5 ml of dimethylformamide. To the suspension was added 56 μl of N,O-bis(trimethylsilyl)acetamide at room temperature with stirring, followed by stirring for 40 minutes.

The solution B cooled to −45° C. was added while stirring to the solution A which had been also cooled to the same temperature, followed by stirring at −45° C. for 1.5 hours and −10° C. for 30 minutes. The reaction solution was charged into 25 ml of ice-cooled 0.5 N hydrochloric acid with stirring and stirred for further 30 minutes. The resulting precipitate was collected by filtration, washed with water, and dried to obtain 83.7 mg of the desired product.

Melting Point: 158°–163° C. (decomposed)

Infrared Absorption Spectrum (cm⁻¹, nujol): 1770, 1660, 1610

NMP Spectrum (δ, DMSO-d₆): 1.31 (6H, t, J=7 Hz), 3.52 (1H, d, J=18 Hz), 3.64 (1H, d, J=18 Hz), 4.08–4.56 (6H, m), 4.97 (1H, d, J=4.5 Hz), 5.28 (2H, s), 5.60–5.82 (2H, m), 6.71 (2H, d, J=8 Hz), 7.25 (2H, d, J=8 Hz), 8.02 (1H, s), 8.18 (1H, s), 9.02 (1H, s), 9.36 (1H, d, J=8 Hz), 9.95 (1H, d, J=8 Hz)

| Antibacterial Activity (MIC, μg/ml) | |
| --- | --- |
| Staphylococcus aureus 209-P | 6.25 |
| Escherichia coli NIHJ | 0.4 |
| Klebsiella pneumoniae EK-6 | ≧0.05 |
| Proteus morganii EP-14 | 1.56 |
| Pseudomona aeruginosa EP-172 | 0.8 |
| Serratia marcescens ES-75 | ≧0.05 |

The following compound was synthesized in the same manner as described above.

(B) 7β-[D-2-(6,7-Dihydroxychromone-3-carboxyamido)-2-(4-hydroxyphenyl)acetamido]-3-[(1-carboxymethyl-5-tetrazolyl)thiomethyl]-cephem-4-carboxylic acid Melting Point: 230°–231° C. (decomposed)

Infrared Absorption Spectrum (cm⁻¹, nujol): 1770, 1664, 1615

NMR Spectrum (δ, DMSO-d₆): 3.50 (1H, d, J=18 Hz), 3.72 (1H, d, J=18 Hz), 4.21 (1H, d, J=14 Hz), 4.48 (1H, d, J=14 Hz), 5.00 (1H, d, J=5.5 Hz) 5.30 (2H, s), 5.6–5.9 (2H, m), 6.75 (2H, d, J=9 Hz), 7.00 (1H, s), 7.26 (2H, d, J=9 Hz), 7.44 (1H, s), 8.86 (1H, s), 9.38 (1H, d, J=8 Hz), 10.26 (1H, d, J=7.5 Hz)

| Antibacterial Activity (MIC, μg/ml) | |
| --- | --- |
| Staphylococcus aureus 209-P | 3.13 |
| Escherrichia coli NIHJ | 0.4 |
| Klebsiella pneumoniae EK-6 | ≧0.1 |
| Proteus morganii EP-14 | 12.5 |
| Pseudomonas aeruginosa EP-172 | 0.8 |
| Serratia marcescens ES-75 | ≧0.1 |

What is claimed is:

1. An N-(substituted chromone-3-carbonyl)phenylglycine derivative represented by the formula

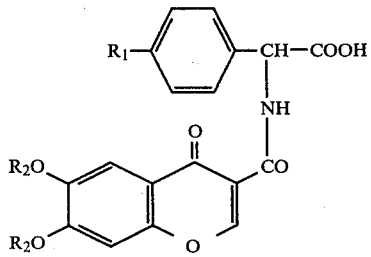

in which R₁ represents a hydrogen atom or a hydroxyl group, and each R₂ represents a hydrogen atom, an alkoxycarbonyl group or a chlorine-substituted alkoxycarbonyl group.

2. The compound as claimed in claim 1, wherein R₂ is a hydrogen atom, an ethoxycarbonyl group or a 2,2,2-trichloroethoxycarbonyl group.

3. The compound as claimed in claim 2, which is D-2-(6,7-dihydroxychromone-3-carboxamide)-2-(4-hydroxyphenyl) acetic acid.

4. The compound as claimed in claim 2, which is D-2-[6,7-bis(ethoxycarbonyloxy)chromone-3-carboxamide]-2-(4-hydroxyphenyl)acetic acid.

5. The compound as claimed in claim 2, which is D-2-[6,7-bis(ethoxycarbonyloxy)chromone-3-carboxamide]-2-phenylacetic acid.

* * * * *